(12) United States Patent
Liu et al.

(10) Patent No.: US 10,894,168 B2
(45) Date of Patent: Jan. 19, 2021

(54) AUTOMATED EXTERNAL DEFIBRILLATOR WITH SHORTENED PAUSE FOR RHYTHM ANALYSIS

(71) Applicant: KONINKLIJKE PHILIPS N.V., Eindhoven (NL)

(72) Inventors: Chenguang Liu, Bothell, WA (US); Eric Grant Halsne, Kenmore, WA (US); Stacy Earl Gehman, Seattle, WA (US); Dawn Blilie Jorgenson, Mercer Island, WA (US); Vijay Aditya Tadipatri, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 158 days.

(21) Appl. No.: 16/089,195

(22) PCT Filed: Mar. 30, 2017

(86) PCT No.: PCT/EP2017/057564
§ 371 (c)(1),
(2) Date: Sep. 27, 2018

(87) PCT Pub. No.: WO2017/167891
PCT Pub. Date: Oct. 5, 2017

(65) Prior Publication Data
US 2019/0105504 A1    Apr. 11, 2019

Related U.S. Application Data

(60) Provisional application No. 62/315,093, filed on Mar. 30, 2016.

(51) Int. Cl.
*A61N 1/39* (2006.01)
*A61B 5/04* (2006.01)
(Continued)

(52) U.S. Cl.
CPC .......... *A61N 1/39044* (2017.08); *A61B 5/046* (2013.01); *A61B 5/04012* (2013.01);
(Continued)

(58) Field of Classification Search
CPC .............. A61N 1/39044; A61N 1/3987; A61N 1/3925; A61N 1/3993; A61B 5/726; A61B 5/046; A61B 5/7217; A61B 5/04012
See application file for complete search history.

(56) References Cited

U.S. PATENT DOCUMENTS 6,671,547 B2  12/2003  Lyster et al.
7,171,269 B1   1/2007  Addison et al.
(Continued)

FOREIGN PATENT DOCUMENTS

WO  2013003852 A1  1/2013
WO  2016091948 A1  6/2016

*Primary Examiner* — Nathan J Jenness

(57) ABSTRACT

An automated external defibrillator (AED) is described which includes two electrocardiogram (ECG) analyzers. One of the ECG analyzers is suitable for use only for ECG which is signal-noise-free, and thus may be used during "hands-off" analysis periods in which no cardiopulmonary resuscitation (CPR) compressions can be provided. The length of the "hands-off" analysis period can be shortened by use of the second ECG analyzer in concert with the first ECG analyzer. Thus, a greater proportion of CPR time through the course of a cardiac arrest rescue is achieved.

14 Claims, 11 Drawing Sheets

(51) Int. Cl.
*A61B 5/00* (2006.01)
*A61B 5/046* (2006.01)
*A61H 31/00* (2006.01)

(52) U.S. Cl.
CPC ............ *A61B 5/726* (2013.01); *A61B 5/7217* (2013.01); *A61N 1/3925* (2013.01); *A61N 1/3987* (2013.01); *A61N 1/3993* (2013.01); *A61B 2505/01* (2013.01); *A61H 31/005* (2013.01); *A61H 2201/0188* (2013.01); *A61H 2201/5043* (2013.01); *A61H 2201/5048* (2013.01); *A61H 2230/045* (2013.01)

(56) References Cited

U.S. PATENT DOCUMENTS

| | | |
|---|---|---|
| 2002/0133197 A1 | 9/2002 | Snyder et al. |
| 2004/0162585 A1 | 8/2004 | Elghazzawi et al. |
| 2011/0224746 A1 | 9/2011 | Didon |
| 2015/0165223 A1 | 6/2015 | Babaeizadeh et al. |
| 2016/0015991 A1 | 1/2016 | Firoozabadi et al. |

AUTOMATED EXTERNAL DEFIBRILLATOR WITH SHORTENED PAUSE FOR RHYTHM ANALYSIS

CROSS-REFERENCE TO PRIOR APPLICATIONS

This application is the U.S. National Phase application under 35 U.S.C. § 371 of International Application No. PCT/EP2017/057564, filed on Mar. 30, 2017, which claims the benefit of U.S. Provisional Patent Application No. 62/315,093, filed on Mar. 30, 2016. These applications are hereby incorporated by reference herein.

BACKGROUND

This invention relates to an improved apparatus and method for treating victims of cardiac arrest, and in particular for those patients who require a treatment regime consisting of cardiopulmonary resuscitation (CPR) and defibrillation electrotherapy.

A defibrillator delivers a high-voltage impulse to the heart in order to restore normal rhythm and contractile function in patients who are experiencing arrhythmia, such as ventricular fibrillation ("VF") or ventricular tachycardia ("VT") that is not accompanied by spontaneous circulation. There are several classes of defibrillators, including manual defibrillators and automated external defibrillators ("AEDs"). AEDs differ from manual defibrillators in that AEDs can automatically analyze the electrocardiogram ("ECG") rhythm to decide if defibrillation is necessary. After deciding that a shock is needed, the AED arms itself for delivering an electrotherapeutic shock, and then the AED advises the user to press a shock button to deliver the defibrillation shock. An AED that operates in this manner is called semi-automatic. Fully automatic AEDs deliver the defibrillation shock without any user input. Fully automatic AEDs are generally called fully automatic defibrillators in order to reduce confusion in terminology.

FIG. 1 is an illustration of a defibrillator 1 being applied by a user 2 to resuscitate a patient 4 suffering from cardiac arrest. The defibrillator 1 may be in the form of an AED or a fully automatic defibrillator capable of being used by a first responder. The defibrillator 1 may also be in the form of a manual defibrillator for use by paramedics or other highly trained medical personnel. Two or more electrodes 6 are applied across the chest of the patient 4 by the user 2 in order to acquire an ECG signal from the patient's heart. The defibrillator 1 then analyzes the ECG signal for signs of arrhythmia with a shock analysis algorithm. Only if a shockable rhythm, such as VF or a non-perfusing ventricular tachycardia (VT), is detected does the defibrillator 1 arm itself to deliver a high voltage shock. The defibrillator 1 signals the user 2 via aural or visual prompts that a shock is advised. The user 2 then presses a shock button on the defibrillator 1 to deliver a defibrillation shock.

It is well established that the quicker that circulation can be restored (via CPR and defibrillation) after the onset of VF, the better the chances that the patient will survive the event. For this reason, many AEDs such as the one shown in FIG. 1 also incorporate a user interface including audible, aural, and visual prompting for guiding a user through a programmed sequence of CPR and defibrillation shocks. The user interface may include detailed aural prompting for properly applying CPR compressions, an audible metronome for guiding the user to the proper rate of compressions, a visual display to show the state and progress of the event, annunciators, flashing lights, and the like. The sequence is pre-programmed into the device in accordance with a protocol established by the local medical authority.

There are several ECG analysis algorithms which automatically analyze a patient's ECG to decide if a defibrillating shock is appropriate to treat the underlying cardiac rhythm. One such algorithm is generally described by Lyster et al. in the co-assigned U.S. Pat. No. 6,671,547 entitled "Adaptive analysis method for an electrotherapy device and apparatus" and herein incorporated by reference. The described algorithm relates to the Patient Analysis System (PAS) algorithm that is currently employed in AEDs, such as the Heartstart™ FR3 AED manufactured by Koninklijke Philips, N.V. of Andover, Mass.

But PAS and similar ECG algorithms for determining a shockable condition require relatively noise-free ECG signals. PAS thus requires the cessation of CPR during analysis because CPR causes artifact in the ECG which can mask VF when it is occurring, or can appear as VF when VF is not occurring. The former condition causes an undesirable reduction in sensitivity of the analysis, while the latter condition causes an undesirable reduction in specificity of the analysis. Consequently, all existing protocols of CPR and defibrillation require periodic "hands-off" periods of at least several seconds to allow the defibrillator to analyze the ECG with sufficient accuracy to be safe, useful, and effective to the patient.

Several problems arise from the need to interrupt CPR for ECG analysis. It has been shown that interruptions in CPR compressions, even for just a few seconds, may reduce the likelihood of a successful resuscitation. Thus, the required cessation of CPR for ECG analysis prior to delivering a defibrillating shock may reduce the chances of a successful patient outcome. In summary, the hands-off time that is necessary for ECG analysis should be minimized in order to improve outcomes.

Several prior art solutions to this problem have been developed, all directed toward reducing the amount of delay between the cessation of CPR and the delivery of electrotherapy. One solution, for example, is to develop an ECG analysis algorithm which can be used in the presence of CPR noise artifact, and thus can reduce or eliminate the need for a "hands-off" analysis period. One such ECG analysis technique involves the wavelet transform analysis of ECG data streams. Such an approach is described by Addison in U.S. Pat. No. 7,171,269 entitled "Method of Analysis of Medical Signals" and incorporated herein by reference. The '269 patent describes the use of wavelet transform analysis to decompose signals into heart and CPR-related signals. Another example of this approach is adopted by Coult et al. in International Patent Application No. PCT/US2012/045292 entitled "Systems and Methods for Analyzing Electrocardiograms to Detect Ventricular Fibrillation." There, an electrocardiogram signal is interrogated by a wavelet, such as a Morlet, Myers, or Mexican Hat wavelet, prior to being analyzed and stratified into a shockable or non-shockable ECG.

Unfortunately, many of the ECG analyzing techniques lack the accuracy necessary to reliably determine a shockable rhythm in the presence of CPR noise artifact, i.e. have insufficient sensitivity, while avoiding "false positive" shock decisions, i.e. have insufficient specificity. These techniques are also susceptible to external electrical noise, such as line noise, and have not been adopted. Because an accurate ECG analysis is very important to treating a patient properly, there is a continued requirement for periodic quiet and artifact-free periods, which of course also require "hands-off" time.

The PAS algorithm is arranged to operate only on a noise-free ECG data stream. If the underlying ECG rhythm is shockable, the PAS algorithm may require just a single five-second data buffer to arrive at a shock decision. Thus, the time between the end of CPR and delivery of a shock may be as short as five seconds.

If the underlying ECG rhythm is non-shockable however, then PAS requires an additional five second data buffer to arrive at a no-shock advised NSA decision for reasons of algorithm specificity and sensitivity requirements. If the underlying ECG signal contains CPR compressions noise or is contaminated with patient motion artifact, PAS may also require one or more additional ECG data buffers to make a decision that meets its required accuracy and specificity. Thus, for other than shockable ECG rhythms, PAS requires at least 10 seconds of "hands-off" time to make such a determination.

What is needed is an improved method and apparatus that reduces the "hands-off" time needed for an ECG analysis. This need is in particular needed for conditions in which the underlying ECG rhythm is non-shockable or contaminated despite the hands-off directives. Such an improvement also should not increase "hands-off" time for other types of ECG rhythms.

SUMMARY

The inventors have recognized the limitations afforded by the prior art, and have discovered a technique to eliminate the second and following ECG data buffers, i.e. the extended analyses, that are required by a "hands-off" analysis such as PAS. In particular the inventive method and apparatus enable the use of a single ECG data buffer analysis during the "hands-off" period, where the single buffer analysis can be completed within five seconds. This can be accomplished even if the underlying ECG rhythm is non-shockable or is contaminated with artifact.

In accordance with the principles of the invention, a method for analyzing ECG in quiet conditions is described. The method is particularly directed to the "hands-off" interval between the end of a scheduled CPR compressions period and the completion of a decision as to whether to arm for a defibrillating shock or to advise to continue CPR. The inventive method adopts a technique in which the ECG is analyzed by two different algorithms, each operating on data lying within different frequency bands. A first algorithm, like the aforedescribed PAS, acts on a lower frequency set of data in the ECG data buffer. A second algorithm, which will be described in more detail and is referred to as the Optimized Arrhythmia Recognition Technology (ART) algorithm, uses a generally higher frequency set of data in the ECG data buffer. The algorithms act simultaneously and independently. An inventive selection criteria, subsequently enables a quicker decision during the quiet period, with decision accuracy similar to prior art methods.

In accordance with the principles of the present invention, an automated external defibrillator (AED) 810 for use during cardiopulmonary resuscitation (CPR) comprises an input 812 of an ECG signal, a user interface 818 having at least one of an aural instruction output and a visual display, a first ECG analyzer 831 in communication with the input and operable to determine a shockable cardiac rhythm during a hands-off period characterized by no presence of CPR-related signal noise artifact from the input, and a second ECG analyzer 832 in communication with the input and operable to determine a shockable cardiac rhythm in the presence of CPR-related signal noise artifact from the input.

A processor 834 is in communication with the user interface, the first ECG analyzer and the second ECG analyzer. The processor is operable to execute software instructions to reduce a duration of the hands-off period only if both of the first and second ECG analyzers determine that a shockable cardiac rhythm is not present. The processor is further operable to execute software instructions to issue a user prompt to end the hands-off period and to resume CPR at the end of the reduced-duration hands-off period.

In other embodiments of the apparatus, a second sequential ECG buffer may be used by the first ECG analyzer to determine a shockable cardiac rhythm. Alternatively, a decision that a shockable cardiac rhythm is not present may be determined from the single ECG buffer. The hands-off period may thus be reduced in some conditions from ten seconds to about five seconds duration.

In an alternative embodiment, the second ECG analyzer may additionally act upon an ECG buffer that occurs during a CPR compressions period just prior to the hands-off period. The AED may subsequently determine that a shockable cardiac rhythm is not present based upon the ECG buffer analysis prior to hands-off period and an analysis on the single ECG buffer that occurs during the hands-off period.

Further in accordance with the principles of the present invention, a method for controlling a defibrillator during the application of CPR comprises the steps of providing a defibrillator having a first ECG analyzer operable to determine a shockable cardiac rhythm during a hands-off period characterized by no presence of CPR-related signal noise artifact, and a second ECG analyzer operable to determine a shockable cardiac rhythm in the presence of CPR-related signal noise artifact, receiving an ECG signal data stream from two or more external electrodes in electrical contact with a patient and in communication with the first and second ECG analyzers, the ECG signal data comprising a cardiac signal, prompting with one of an audible or visual output instructions for providing successive periods of CPR wherein the ECG signal is characterized by corruption from a CPR compressions noise artifact and hands-off periods wherein the ECG signal is characterized by a lack of CPR compressions noise artifact. The method continues with the step of analyzing the cardiac signal with the first ECG analyzer during a hands-off period, and analyzing the cardiac signal with the second ECG analyzer. The method continues with the step of reducing the duration of the hands-off period to a reduced-duration hands-off period only if both of the first and second ECG analyzers determine that a shockable cardiac rhythm is not present, and then issues audible or visual output instructions for ending the hands-off period and/or for resuming CPR at the end of the reduced-duration hands-off period.

In a further embodiment, the method may incorporate a hands-off period that consists of two or more ECG data buffers each of a predetermined length, and wherein the reduced-duration hands-off period is one ECG data buffer in duration. The hands-off period may be about ten (10) seconds in length, and the reduced-duration hands-off period is about five (5) seconds in length.

In an alternative embodiment of the method, the second ECG analyzer may additionally act upon an ECG buffer that occurs during a CPR compressions period just prior to the hands-off period. The method may subsequently determine that a shockable cardiac rhythm is not present based upon the ECG buffer analysis prior to hands-off period and an analysis on the single ECG buffer that occurs during the hands-off period.

As used herein for purposes of the present disclosure, the term "processor" is used generally to describe various apparatus relating to the operation of a medical apparatus, system, or method. A processor can be implemented in numerous ways (e.g., such as with dedicated hardware) to perform various functions discussed herein. A processor is also one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more computer storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In various implementations, the terms "low-power standby circuit", "clock", "state change monitor", "comparator" apply to components that are generally known in the art, and may be embodied in conventional microprocessors, application specific integrated circuits (ASICs), and field-programmable gate arrays (FPGAs), or may be integrated into the above described processor or controller. "Outputs" and "signals" may be understood to be electrical or optical energy impulses which represent a particular detection or processing result.

IN THE DRAWINGS

DETAILED DESCRIPTION OF THE INVENTION

A shock advisory algorithm that may be adopted by this invention is called the Optimized Arrhythmia Recognition Technology (ART). This algorithm generally applies the principles of the afore-mentioned wavelet transform analysis to a stream of ECG signals, but instead replaces the wavelet transform with a series of fixed-frequency band pass filters. The set of band pass filters is preferably constructed to have frequency windows shaped like the Gaussian windows that are used to produce traditional Morlet wavelets. The following description mentions the suppression of CPR artifact related noise using the ART algorithm. However, the inventors note that the ART algorithm may also be used in a quiet, hands-off, period of analysis without modification. Such use of ART during quite periods in which no CPR artifact related noise is present is indeed directed by the method and apparatus of this invention.

The ART algorithm suppresses CPR artifact related noise by selectively passing relatively high frequency components of a potentially corrupted ECG signal. ART is based on the inventors' realization that, while CPR and an organized cardiac rhythm can occur at similar repetition rates of about 1 to 2 Hz, typical CPR noise has relatively few high frequency components in its signal, i.e. the signal tends to be a rounded waveform. Cardiac activity tends to have relatively numerous high frequency components due to the rapid polarization and depolarization of the heart over a single cycle. It is these high frequency components that are to be captured and analyzed by ART.

Figure 1:
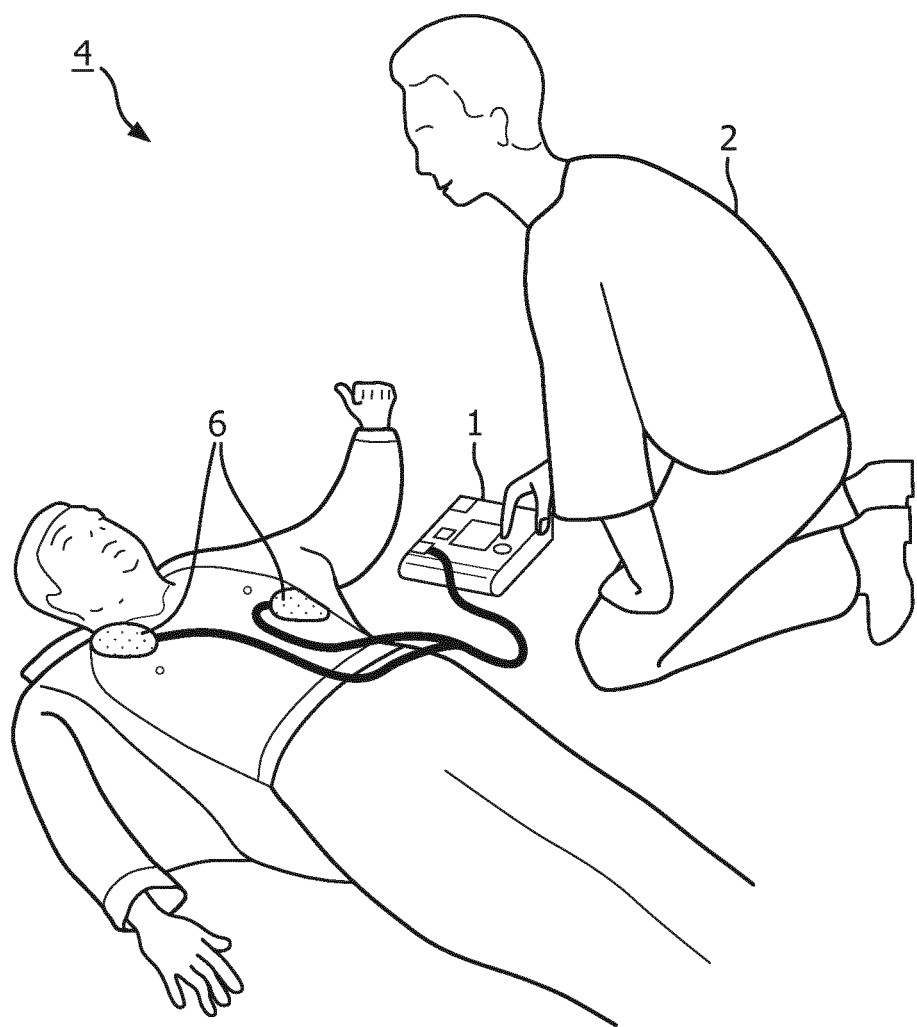
FIG. 1 illustrates a defibrillator and its use during a cardiac rescue, according to the prior art.
Figure 2A:
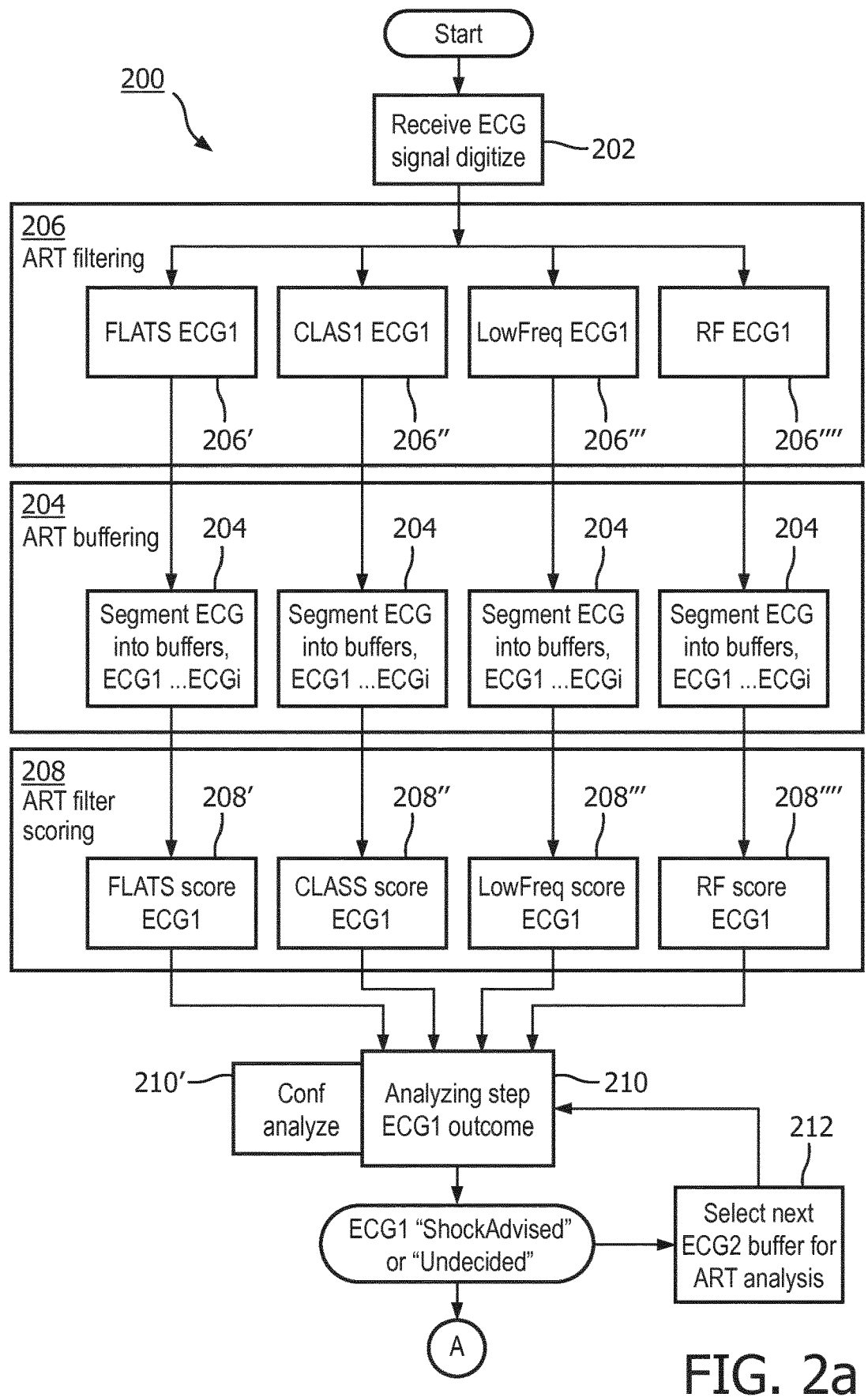
FIG. 2a illustrates one process flow embodiment of the inventive algorithm for analyzing ECG in the presence of noise artifact from CPR compressions.

Now turning to the illustrations, FIG. 2a illustrates a process flow embodiment of the inventive ART algorithm 200 for analyzing ECG in the presence of noise artifact from CPR compressions. At step 202, the method first receives an ECG signal, preferably from two or more electrodes which are arranged in electrical contact with a patient's skin. The ECG signal is a time-varying voltage whose source is the patient's heart as well as possibly voltages induced by CPR compressions being applied to the patient. The signal may also include other artifact signals that are external to the patient, such as patient jostling and motion, external electrical noise, etc. The ECG signal is preferably digitized into a stream of signal data.

At filtering step 206, the digitized ECG signal stream is processed through the ART filtering algorithm. Here, each data point in the signal stream is filtered through a set of first through fourth parallel filters at first through fourth parallel filtering steps 206' 206" 206" and 206"", each having a different band-pass characteristic. Each filter is preferably a Finite Impulse Response filter. The number of filters and the band-pass characteristics of each filter may differ somewhat within the scope of the invention.

Figure 3:
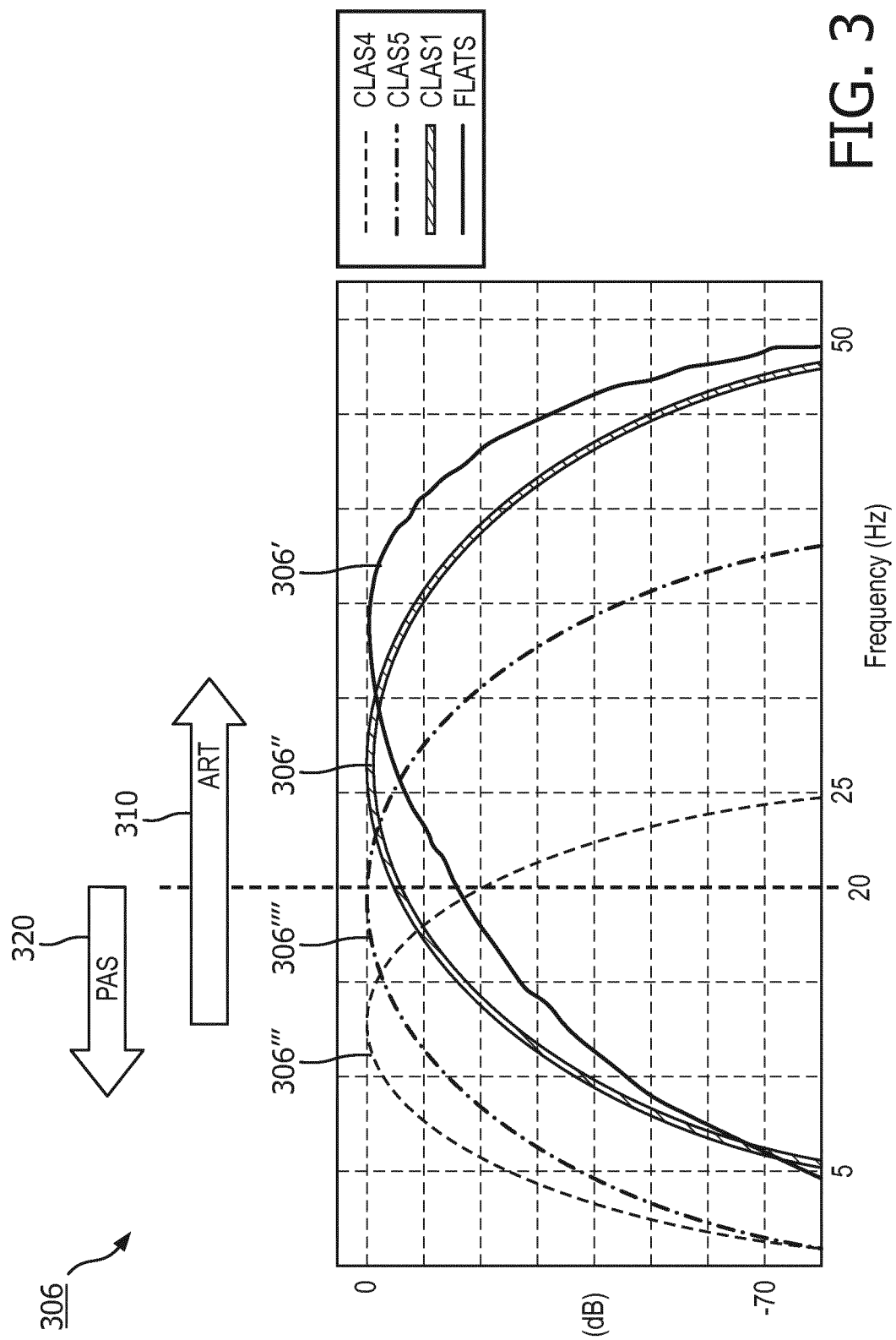
FIG. 3 illustrates the frequency ranges of ECG of primary use to a first ECG analysis algorithm and a second ECG analysis algorithm, according to the present invention.

A preferred arrangement of ART filters 306 is as follows and is shown in FIG. 3. Four basic filters may be adopted, which generally apply to the corresponding filter steps 206 in FIG. 2a. One, called FLATS 306', and another one, called CLAS1 306", tend to pass higher frequency components of the ECG signal, and may present features to 1) distinguish ventricular fibrillation from asystolic rhythms; 2) distinguish ventricular fibrillation from organized cardiac activities; 3) distinguish ventricular fibrillation from asystolic rhythms and organized cardiac activities. Both FLATS 306' and CLAS1 306" tend to attenuate data at frequencies associated with CPR artifact such that their outputs are of cardiac information that is separated from the CPR compression noise signal. As can be seen in the illustrative and exemplary embodiment of FIG. 3, FLATS 306' has a center frequency of about 35 Hz, and CLAS1 306" has a center frequency of about 25 Hz. CLASS 306"" is arranged to reject radio frequency (RF) noise. And CLAS4 306'" may be arranged to pass lower frequency components that are useful for rejecting false positive indications of VF caused by certain artifacts, for instance, due to transportation, muscle contraction, radio frequency interference, etc. In the preferred arrangement, the digitized ECG signal input results in four filtered ECG signal stream outputs.

Also illustrated in FIG. 3 is a comparison of the primary ranges of frequency in the ECG signal as used by ART 310 and the frequency range of a first ECG algorithm 320, such as PAS. Because PAS is optimal for use with a frequency band under twenty (20) Hertz, it can easily be seen that different sets of ECG signal data from the same ECG signal, or data buffer, are used by each of the two analysis algorithms. This indicates that the decisions from the first and second ECG analyzers, which adopt the first and second ECG analysis algorithms, are somewhat independent.

Figure 4:
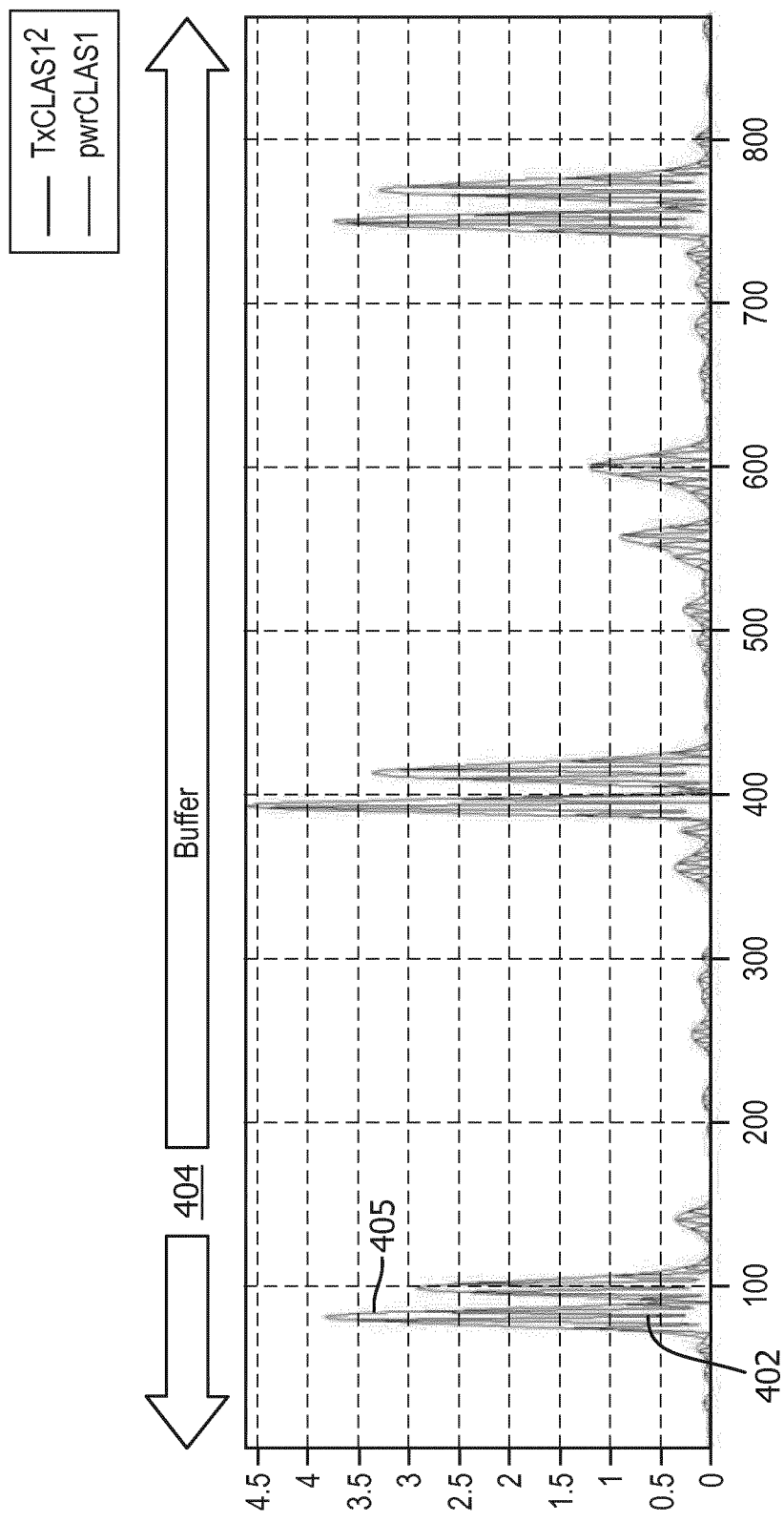
FIG. 4 illustrates an example ECG output buffer from one of the filters for a second ECG analysis algorithm shown in FIG. 3, according to one embodiment of the present invention.

As can be seen from FIG. 4, many oscillations exist in the filtered signals, so that there are many zero and near-zero samples in the buffer. In order to remove these effects, an additional envelope filter may optionally be applied to the data in order to remove the localized zeros and non-zeros. FIG. 4 illustrates the effects and the optional envelope filtering step 405 on the oscillating output 402 of the CLAS1 filter 306".

At buffering step 204, each stream of filtered ECG signal data is segmented into sequential time segments, i.e. buffers ECG1 ECG2 . . . ECGi. One preferred arrangement is non-overlapped adjoining buffers of 3.5 seconds length. One sampling rate is 250 samples per second, which equates to 875 samples of ECG per buffer. Time segment length and sampling rates are predetermined, and may differ within the scope of the invention. Each of the data points from each buffer has a value, depending on the input and the underlying filter. An example of a filtered ECG buffer data set for CLAS1 is shown in FIG. 4.

It is preferred and advantageous that the buffering step 204 occurs after the filtering step 206. By filtering prior to buffering, the method avoids filter transients at the edge of each buffer. Otherwise, the method would require longer, overlapping buffers which would entail longer analyzing time with the attendant dilatory effects on patient outcomes.

At step 208, data in each of the filtered ECG buffers is compared to a threshold value. The number of data points falling within the threshold value for that filtered ECG buffer, called a score, is then calculated for use by the analyzing step 210. Of course, any mathematical equivalent to the number of data points, such as a proportion or a fraction, could be substituted within the scope of this method step. For the purposes of this illustration, the score for the filtered ECG buffer for the FLATS filter is designated the FLATS score. The score for the filtered ECG buffer for CLAS1 is designated the CLAS score. Accordingly, FIG. 2a illustrates that threshold comparisons step includes a threshold comparison for each of the parallel filtering steps, i.e. first through fourth parallel threshold comparison steps 208', 208", 208'", and 208"".

Threshold values for each of the filtered ECG buffer scores may be arrived at in a number of ways, the determinations of which fall within the scope of the present invention. Thresholds may be fixed, e.g. predetermined, or may be adaptive, e.g. are calculated based upon a mean value of all of the data points in the particular buffer. For example, the FLATS buffer data set may be scored against a fixed threshold value, and the CLAS buffer data set may be scored against an adaptive threshold value.

Figure 5:
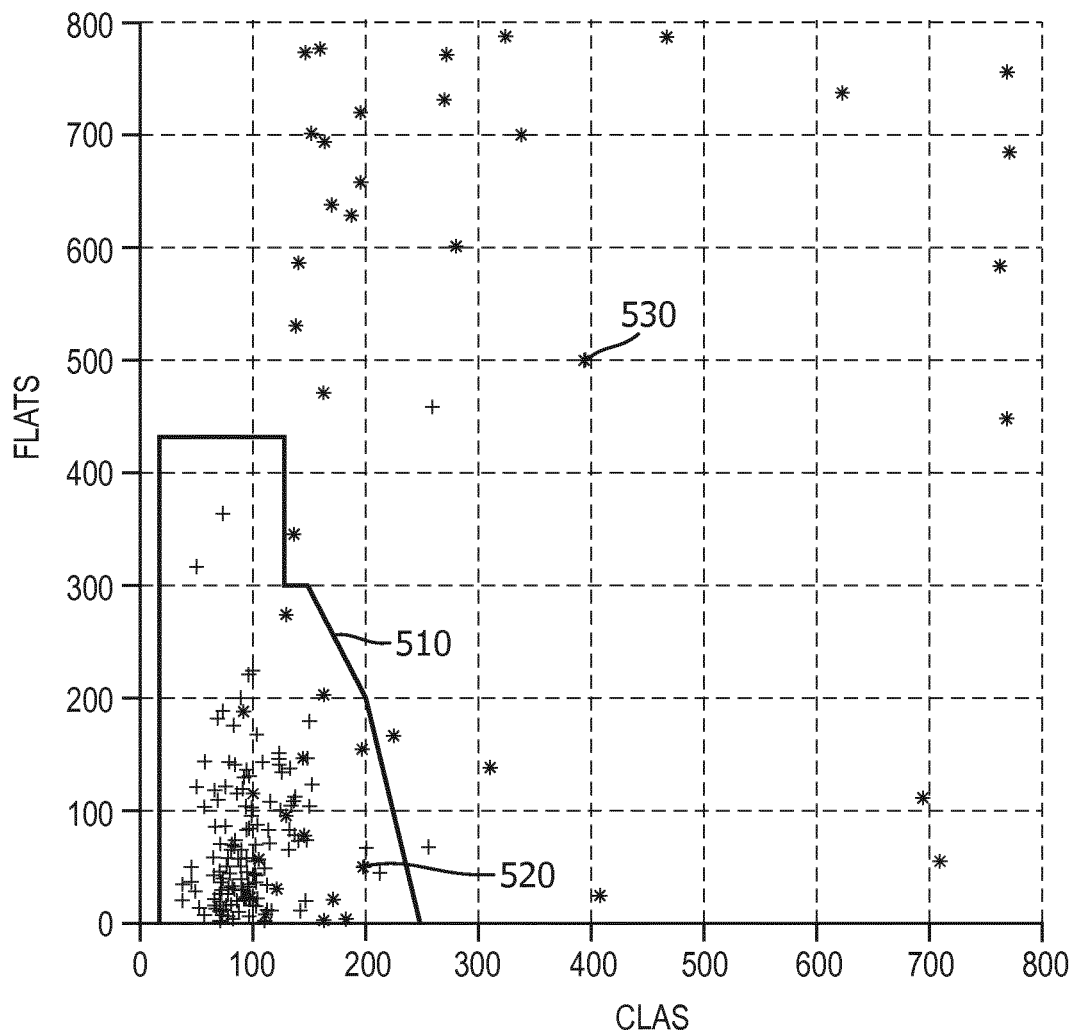
FIG. 5 illustrates an exemplary two-dimensional decision surface for classifying an ECG signal as VF or undecided in a second ECG analysis algorithm, according to one embodiment of the invention.

The analyzing step 210 begins by comparing the filtered ECG buffer scores to a predetermined decision surface. The decision surface, which is constructed using databases of ECG signal data having CPR corruption noise, defines whether a given set of buffer scores indicates "VF" or "undecided", i.e. other than VF. One example of a decision surface in the CLAS and FLATS dimensions is illustrated in FIG. 5. In that example, decision surface 510 is constructed of corresponding pairs of one of the CLAS scores and FLATS scores. Score pairs that fall within the decision surface 510 indicate a VF condition. Score pairs that fall outside the decision surface 510 indicate an undecided condition. Additional dimensions of decision surface may be added using threshold values for additional filtered ECG buffers as desired to create a more accurate VF decision. Although only two dimensions are shown here, three or more dimensions may be used for a decision surface that incorporates the other CLAS scores as well.

Analyzing step 210 proceeds by comparing two or more buffer scores that represent the particular cardiac signal characteristics to the decision surface in order to determine VF or other than VF. For the example shown in FIG. 5, an example pair of CLAS/FLATS score is shown at 520, indicating VF. The value pair 530 that falls outside the decision surface 510, e.g. above and/or to the right, indicates an undecided, i.e. other than VF, condition.

Each original time-segmented ECG buffer can thus be designated as "shock advised", i.e. corresponding to VF, or "undecided", i.e. corresponding to "other than VF". Once the ECG buffer is determined as shock advised or undecided, ART repeats the steps of capturing, obtaining, filtering, and analyzing for the next ECG buffer in the time sequence as shown in "select next ECG buffer" step 212. The process of repeating enables additional methods of combining each new buffer with previous buffers to generate an overall continuous determination of the presence of VF or not.

The above-described method has been shown to identify VF with an accuracy that is sufficient to safely make a shock determination during the application of CPR, and without the need for further confirmation of the analysis during a "hands-off" time. The sensitivity of ART to VF for a single buffer of CPR-contaminated ECG has been demonstrated to exceed 70%, i.e. ART will detect true VF more than 70% of the occurrences. Similarly, the specificity of ART has been demonstrated to exceed 95% for a single buffer of ECG, i.e. will not generate a false positive VF indication from more than 95% of "other than VF" occurrences.

It may also be noted that the ART performance during "quiet" periods approaches that already demonstrated in the existing PAS algorithm. The sensitivity of ART to VF on ECG data that is not contaminated with CPR artifact exceeds 80%, as compared to PAS on similar data at about 94%. Specificity of ART and PAS to false VF on a buffer of "clean" ECG is nearly identical. Thus, ART may also be used successfully and accurately during hands-off analysis periods.

Figure 2B:
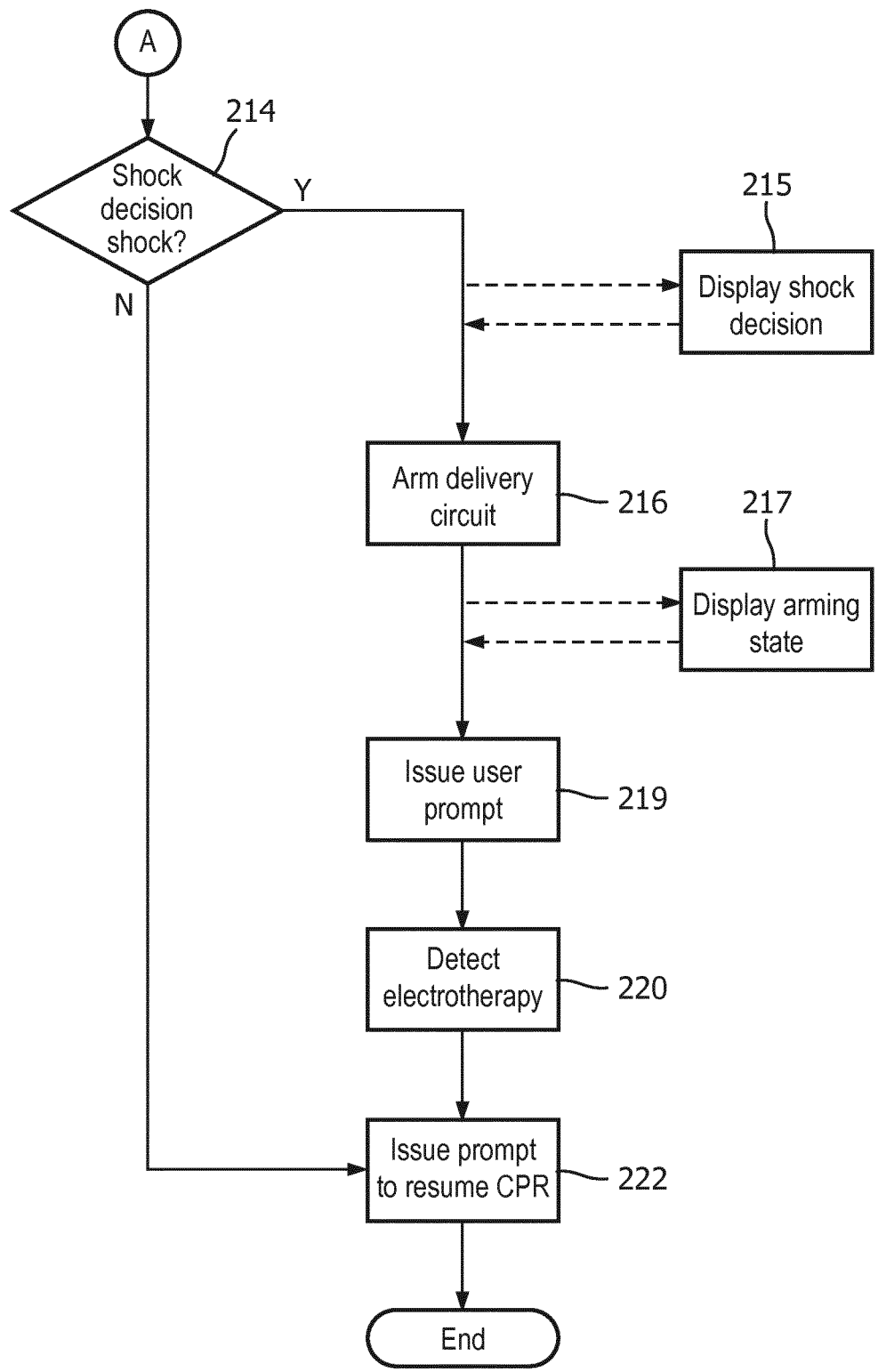
FIG. 2b illustrates a process flow for determining a shockable cardiac rhythm from the analyzed ECG, according to one embodiment of the present invention.

Now turning to FIG. 2b, the method continues. One preferred embodiment of the method comprises the aforedescribed steps 202-212 as being performed in a separate processor, such as a DSP, from the steps mentioned in the following several paragraphs. Such an arrangement allows each ECG buffer in turn to be analyzed and classified as VF or "undecided" relatively independently of the shock decision and control processor, which primarily needs only the stream of classifications data from the ECG signal stream. Another preferred embodiment of the method comprises further separation of processing into multiple components. For example, digitization of the ECG signal input at step 202 could be handled in a front end chip such as an ASIC, the digital stream fed into a DSP for filtering the digitized ECG signal stream into the separate filtered streams corresponding to method step 206. Yet another processor would then receive the filtered streams for final classification, decision-making, and response handling functions that will be described in the following paragraphs.

If VF is determined from the ECG buffer at analyzing step 210, i.e. a "shock advised" outcome, then the underlying ECG rhythm is generally assumed be a shockable cardiac rhythm. But the optimal response to a VF determination may not simply be to prepare the underlying device to provide electrotherapy. Instead, it may be preferable to obtain confirming determinations, or to otherwise to convey the determination to the user in some manner that does not unduly disrupt the ongoing cardiac rescue. A separate deciding step 214 is thus warranted for these purposes, and is shown in FIG. 2b as taking input from analyzing step 210. Examples of such situations will be provided in following paragraphs.

Because ART sequentially analyzes multiple ECG buffers during a minutes-long CPR period, accumulated sensitivity to an ongoing patient condition of VF will increase, i.e. more chances to detect a true VF condition. But it is also expected that accumulated specificity will decrease, i.e. more chances to mistake an "undecided" condition as VF. In order to maintain the specificity of the overall method at an acceptable level over this relatively long period of time, optional multiple-buffer rules may be developed for making a shock decision from VF/undecided decisions over time-consecutive ECG data buffers. The repeated, second analyzing step 210 of an ECG buffer of a later, second predetermined time segment is provided to the deciding step 214. Deciding step 214 then additionally bases its final decision on the second analyzing step.

For example, the analyzing step 210 may determine that a cardiac rhythm is shockable only if three time-consecutive ECG buffers indicate VF. Otherwise, the analyzing step indicates a non-shockable rhythm. It has been shown that, under these rules, ART maintains a specificity of >95% over long periods of CPR, while sensitivity remains >70%. In some cases, sensitivity can exceed 95% and specificity can exceed 98%. Such performance is acceptable for making shock decisions during CPR periods. In summary, whereas deciding step 214 essentially receives an ongoing stream of VF/undecided ECG buffer, the step 214 applies the rules for the final decision that the underlying device should operably proceed to the delivery of a defibrillating shock.

A displaying step 215 may be initiated immediately upon the determination, such as a visual graphic or textual message on a display, a light signal, or a subtle audible signal. Preferably, the displaying step 215 is provided even before the device is fully prepared to deliver electrotherapy, but in an unobtrusive manner that does not distract the user from continuing CPR compressions up until the device is ready for shock delivery. On the other hand, there are some modes of operation in which it may be preferable not to provide any information at all to the user of a shock determination until arming is complete. Some lay users may be unnecessarily distracted or startled from providing CPR compressions at the mere indication that the device is preparing to deliver a shock.

Responsive to a determination from deciding step 214 that a shockable cardiac rhythm exists and that electrotherapy should be provided, an arming step 216 begins. Arming step 216 may consist of charging a high voltage charging circuit with sufficient energy to defibrillate a patient. Arming step 216 may include an audible and/or visual indicator that the arming step has begun, along with some indication as to the progress toward being fully prepared for shock delivery, step 217. For example, dynamic bar graph indicia on a visual display may show the progressive filling of a bar graph corresponding to the increasing charge state of the high voltage circuit. A text message on display may also indicate that charging is ongoing. An ECG display may be displayed on the charging state display simultaneously with the progress indicators. FIGURE ? illustrates one exemplary embodiment of such a display. An audible progress indicator could comprise a continuous tone of rising frequency which stops when a fully charged state is attained.

At the completion of arming step 216, the electrotherapy device is fully prepared to deliver a shock. After arming, it is preferable that a step of automatically issuing a user prompt 219 to stop CPR for the delivery of electrotherapy occurs. An audible prompt from a speaker 830, an illuminated or flashing shock button light 820, and/or a display indication 802 may be used to signal the user to stop CPR for shock delivery. See FIG. 8 for an example of these indicators on a user interface 818. In the case of an AED, the prompt may also instruct the user to press the shock button 892 to deliver a shock. In the case of a fully automatic defibrillator, a shock may automatically be delivered immediately after the prompt occurs, still at step 219. If the user is employing electrically insulated gloves or other such protective gear, any prompting to "stop CPR" at step 219 may optionally be omitted altogether.

In some circumstances, it may be desirable to delay the issuing of the user prompt to stop CPR at step 219 until a minimum amount of CPR has been provided. For example, it may be desirable to conduct at least 30 seconds of uninterrupted CPR prior to delivering a shock.

Immediately after the delivery of electrotherapy, the user may be automatically prompted to resume CPR at step 222. The device may optionally be enabled to detect the delivery of electrotherapy, at step 220. Detecting delivery can be obtained by sensing outgoing current, a button press, or the like. Then the method process returns to the steps of capturing, obtaining, filtering, and analyzing in accordance with the state of the cardiac rescue.

If ART reaches a non-shock determination at deciding step 214, i.e. a "NO" decision, then the method proceeds directly to prompting step 222. As previously indicated, this prompt should be issued as quickly as possible, in order to reduce detrimental "hands-off" time to the greatest extent possible.

The method steps described above allow CPR to continue right up until the moment of delivering electrotherapy, and then to resume CPR immediately thereafter. The result is that the proportion of "hands-on" time during a cardiac rescue is increased, thereby improving the effectiveness of the overall treatment. Idle time waiting for a "hands-off" ECG analysis can be essentially eliminated, thereby avoiding the loss of blood pressure and flow that occurs so quickly upon cessation of CPR. These benefits can be realized along with the method's ability to treat a reversion to VF during the CPR period. If refibrillation occurs, the method simply detects the VF and prepares for electrotherapy in the midst of the ongoing CPR compressions.

Other advantages are afforded by the inventive method. The inventors have discovered that the use of filters instead of wavelets somewhat reduces the computational load required to analyze for VF, and more effectively suppresses interference by power line noises or similar high-frequency noises. Most of the method steps can thus be accomplished in a single digital signal processor (DSP) that is arranged to receive the ECG signal stream, to process the stream, and then to output a continuous, time aligned and transformed ECG data stream. The DSP can also operate in parallel with a second processor that controls the final shock decision and delivery sequence in the AED. Also, the series of filters can be easily adjusted to also provide more robust rejection of signals induced by DC offsets, 50 Hz and 60 Hz external power-line noise.

Figure 6:
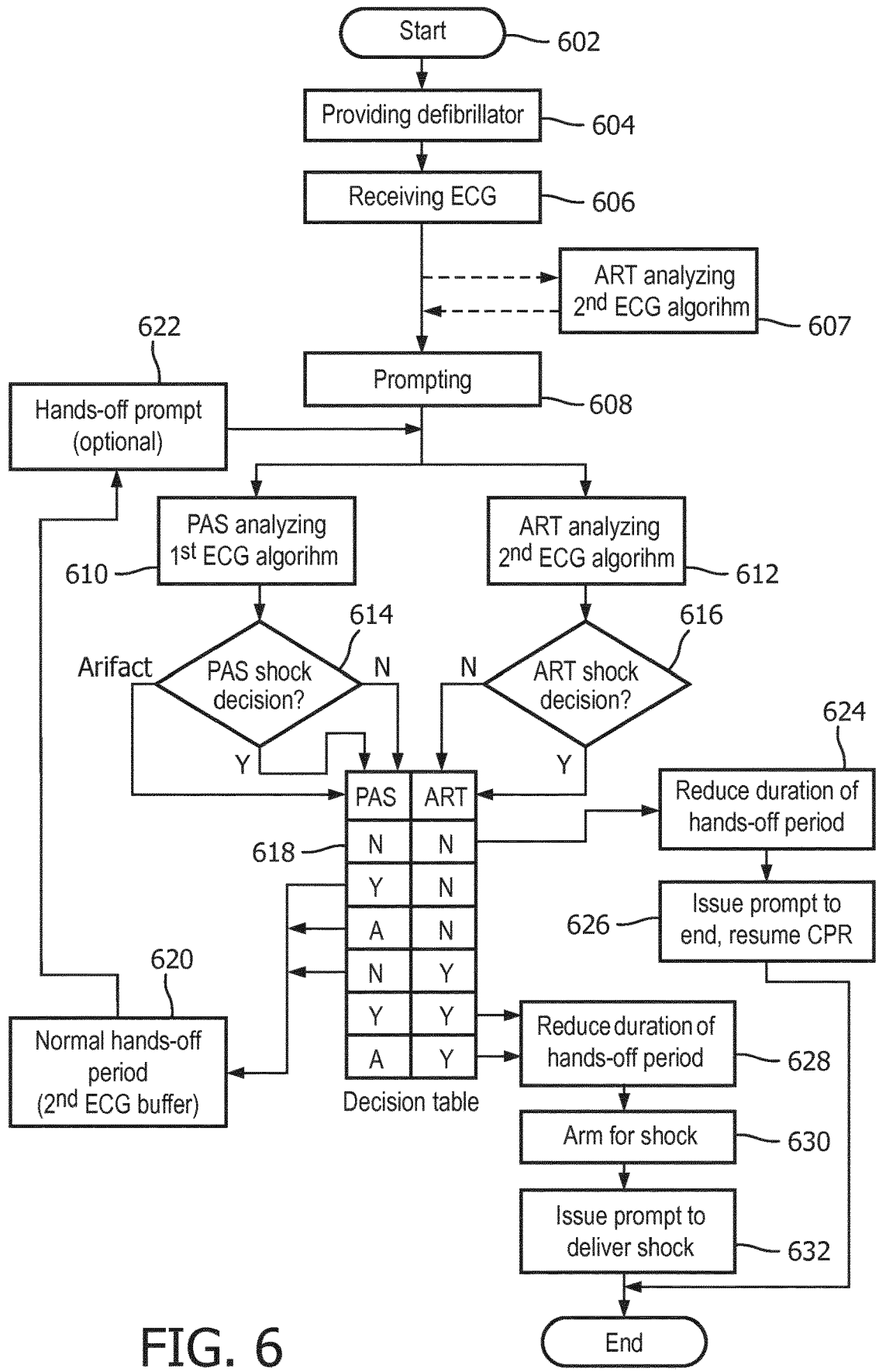
FIG. 6 illustrates a flow chart method, according to one embodiment of the invention.

Now turning to FIG. 6, a method is described for controlling a defibrillator during the application of CPR. The method in particular incorporates shock decisions made by both of the above-described ART ECG analysis algorithm and the known PAS ECG analysis algorithm. Preferably, both algorithms are run simultaneously and during a quiet analysis period that lacks any CPR-related signal noise artifact in the ECG signal.

The method begins at start step 602, at which a decision has been made to use a defibrillator in, for example, a cardiac emergency or for a training session. A source or input of ECG signals is attached to the defibrillator, such as through a set of patient electrodes connected to the defibrillator through lead wires.

At providing step 604, a defibrillator that incorporates two different ECG analyzers is provided. A first ECG analyzer comprises an ECG analysis algorithm, such as the aforementioned PAS, that is particularly operable to automatically determine a shockable rhythm during a hands-off period characterized by a lack of signal noise artifact on the ECG data stream. The output of the first ECG analyzer may be a "shock advised" or a "no shock advised" decision. If the first ECG analyzer detects confounding artifact noise, it may provide an output decision of "artifact."

Providing step 604 also provides a second ECG analyzer. The second ECG analyzer incorporates a second ECG analysis algorithm, such as the aforementioned ART, that is particularly operable to determine a shockable cardiac rhythm in the presence of CPR-related signal noise artifact. The second ECG analyzer may of course also be used during "quiet" periods of no artifact. Because the second ECG analyzer must account for uncertainties caused by artifact, its sensitivity and specificity of decisions may be somewhat lower than of the first ECG analyzer. Both analyzers of course receive inputs from the source of ECG signals.

The method continues at receiving step 606. Both of the first and second ECG analyzers receive an ECG signal data stream from the input, which may be from a pair of electrodes in contact with a patient. Thus, the ECG signal data comprises a cardiac signal.

At the beginning of receiving step 606, CPR compressions may already be in progress or not, depending on the state of the cardiac rescue at that point. Some AED rescue protocols indicate that CPR should be done prior to a first defibrillation: some AED protocols indicate that defibrillation should be accomplished at the outset of the rescue. Depending on the protocol, a prompting step 608 causes the AED to issue audible and/or visual output instructions that may guide the user through successive periods of CPR and defibrillation. The periods of defibrillation are preferably preceded by a prompted hands-off period so that an artifact-free ECG data stream may be evaluated for a shockable rhythm.

It may be seen that the ART-like ECG analysis algorithm may optionally be operating before any prompting step 608. At analyzing step 607, the ART algorithm analyzes the ECG data stream even in the presence of CPR compressions noise artifact, whereupon ART may be able to provide a shock decision for use even prior to the hands-off period.

Prompting step 608 issues an audible and or visual prompt to begin a hands-off period, such as with an instruction to "Stop CPR" and/or to "Don't touch the patient." Thus, the ECG signal presumably then begins to be characterized by a lack of CPR compressions noise artifact.

Figure 7:
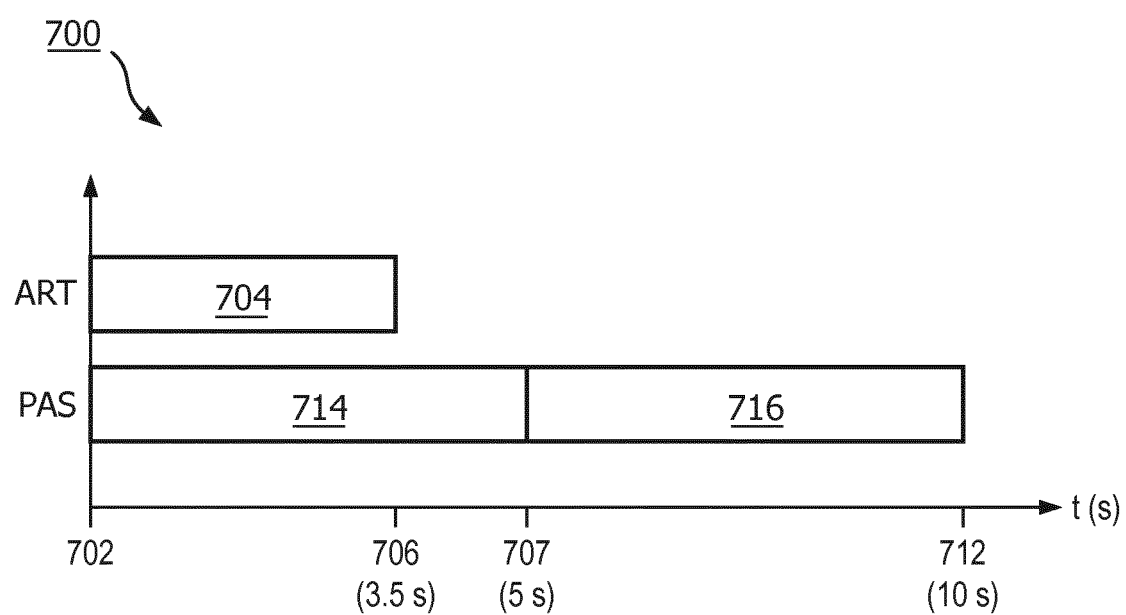
FIG. 7 illustrates a time line of automated decisions made by a defibrillator during operation, according to one embodiment of the invention.

Shortly after the prompting step 608, both of the first and second ECG analyzers begin analyzing the cardiac signal at first analyzing step 610 and second analyzing step 612. The analysis is shown in FIG. 7 starting at start time 702. Step 610 of analyzing the cardiac signal with the first ECG analyzer is preferably performed with an ECG analysis algorithm, such as PAS, that is optimized for use on an artifact-free ECG signal. As can be seen in FIG. 7, the first analysis is preferably performed on sequences of ECG signal data buffers 714, 716 each having a length of about 5 seconds. Other time lengths are envisioned as well, including the overlapping of buffers for a portion of the durations. FIG. 7 also illustrates that the duration of the PAS analysis is typically two ECG data buffers 714 and 716, each having a predetermined length 707, which in this example characterize a total duration 712 of about ten (10) seconds. Ten seconds is thus the minimum length of the hands-off period if using the first analyzing step only. As will be seen, this duration can be shortened substantially by the present invention.

Other ECG analysis algorithms may also be used in this step 610, such as the "Solomon" ECG analysis algorithm used in the Philips MRX defibrillator, manufactured in Andover, Mass.

First analyzer output step 614 issues a decision about each ECG data buffer. Thus, step 614 will sequentially issue decisions as each data buffer analysis is completed, e.g. every five (5) seconds or so. This output step 614 preferably issues one of the following decisions as shown in FIG. 6: "Shock advised" shown by the "Yes" output; "No shock advised" shown by the "No" output, and; "Artifact". "Shock advised" indicates with acceptable statistical confidence the presence of a shockable ECG rhythm. "No shock advised" indicates with acceptable statistical confidence the lack of a shockable ECG rhythm. "Artifact" indicates that signal noise has been detected at levels too high to make a confident shock/no-shock decision. First analyzer output step 614 for each ECG buffer is provided to decision step 618.

Figure 8:
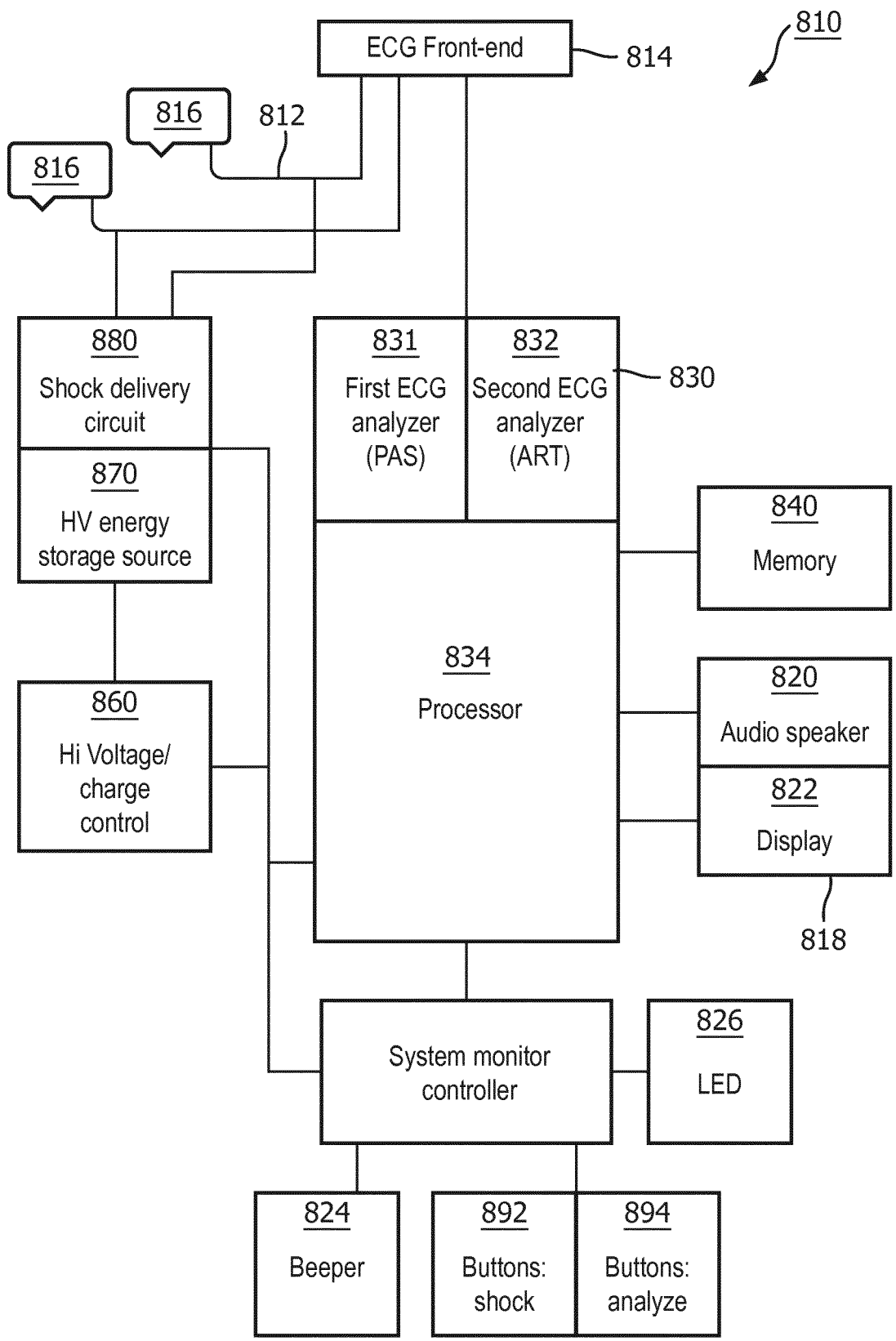
FIG. 8 illustrates a functional block diagram of an external defibrillator according to the present invention.

The second ECG analyzer 832, see FIG. 8, also operates on the ECG data stream at the beginning 702 of the hands-off period and at step 612 of analyzing the cardiac signal with the second ECG analyzer. The second ECG analysis algorithm, such as the afore-described ART algorithm, may be optimized for a different buffer length 706, such as for 3.5 seconds as shown in FIG. 7. The ECG data buffer 704 for the second ECG analyzer is based upon the same data stream as that used by the first ECG analyzer, but may optimize on a different frequency range, see FIG. 3. Second analyzer output step 616 is preferably one of: "Shock advised" as illustrated by the "Yes" output from step 616, or; "Undetermined" as illustrated by the "No" output from step 616. The second analyzer output step 616 is provided to decision step 618 at the end of each 3.5 second ECG data buffer.

Other ECG analysis algorithms may also be used in this step 612, such as the "Vrhythm" ECG analysis algorithm used in the Philips FR2 defibrillator, manufactured in Andover, Mass., or other known ECG algorithms which account for CPR compressions noise artifact in the ECG data stream.

Decision step 618 determines from the first and second ECG analyzers outputs from steps 614 and 616 the conditions for which the hands-off period may be shortened to a reduced-duration hands-off period. The determination by the table shown in step 618 and also in Table 1 below.

appropriate. In particular, if the ECG analyzers at steps 614 and 616 indicate conflicting decisions, i.e. one analyzer indicates "shock advised" and the other analyzer indicates "no shock advised", then a second confirming ECG analysis, e.g. another ECG buffer 716, is needed. If a "no shock advised" output from the second ECG analyzer is accompanied by an "artifact" indication from the first ECG analyzer, then a second confirming ECG analysis, e.g. another ECG buffer 716, is also needed. Decision table step 618 thus maintains the hands-off period at the initial duration at normal duration step 620. If artifact from CPR is indicated, an optional prompting step 622 may follow step 620 to remind the user to keep hands off the patient. Then the method returns to analyzing steps 610, 612.

If a shock decision output at decision step 618 is indicated, and method 600 implements a reduced-duration hands-off period at step 628, then the defibrillator immediately begins arming its high voltage circuitry for a defibrillating shock at arming step 630. Preferably, the method 600 immediately begins an issuing step 632 along with arming step 630. Issuing step 632 comprises audible and/or visual output instructions for ending the hands-off period and for guiding the user to deliver electrotherapy. If the defibrillator is fully automatic, this issuing step 632 advises the user to keep hands off the patient and that a shock is being delivered. After issuing step 632 is complete, the method 600 ends. The ending step may subsequently proceed to another fixed CPR interval or return to step 606 for additional analysis.

TABLE 1

| S (Shock advised), NS (No shock advised, undetermined), A (Artifact) | | | | | | |
|---|---|---|---|---|---|---|
| 2$^{nd}$ ECG, ART output | S | S | S | NS | NS | NS |
| 1$^{st}$ ECG, PAS output | S | NS | A | S | NS | A |
| Determination | Shock | Second buffer needed | Shock | Second buffer needed | No shock | Second buffer needed |
| Reduce duration? | Yes | No | Yes | No | Yes | No |
| New hands-off duration | 5 s. | 10 s. | 5 s. | 10 s. | 5 s. | 10 s. |

As is shown in both tables, several conditions may exist in which a hands-off duration may be shortened. In particular, the condition in which both of the first and second ECG analyzers in analyzing steps 610, 614 and 612, 616 have determined that a shockable cardiac rhythm is not present may enable a reduced-duration hands-off period. The reduced-duration hands-off period may thus comprise just one ECG data buffer, of for example about five (5) seconds in length. The method includes reducing step 624 for this condition.

Other conditions in which a reduced-duration hands-off period may be indicated are also shown in decision step 618 and Table 1. If both ECG analyzers determine a "shock advised" in their respective first ECG data buffer, the duration may be reduced. If the first ECG analyzer cannot make a decision because of artifact, but the second ECG analyzer indicates a shock advised, then the duration may be reduced. The method includes a second reducing step 628 for these conditions. Again a preferable reduced-duration is five (5) seconds. to the long Other conditions at decision table 618 and Table 1 indicate that reducing the hands-off duration is not indicated or Issuing step 626 follows the "no-shock advised" decision from each ECG analyzer and the implementation of the reduced-duration hands-off period at step 624, then the defibrillator processor implements a "resume CPR" issuing step 626. Issuing step 626 comprises issuing instructions for ending the hands-off period and for resuming CPR at the end of the reduced-duration hands-off period, with one of the audible or visual outputs. Preferably, issuing step 626 occurs immediately at the end of the reduced-duration hands-off period. Issuing step 626 should comprise a voice or visual prompt that indicates that no shock is advised and to immediately start CPR. One exemplary voice prompt is "No shock advised, start CPR."

An alternative embodiment of the method uses the second ECG analyzer result that is obtained at optional step 607, i.e. that is conducted during the CPR compressions period that occurs just prior to the hands-off period starting at step 608. The "shock/no-shock" decision step from this step 607 may be provided to decision step 618 in place of the output from steps 612, 616. The remaining steps of method 600 then occur as previously described.

An exemplary performance of a preferred embodiment is now described. The ART and PAS ECG analyzers are applied to the clean annotated rhythms in an ECG development database. The PAS single-buffer analysis requires 5 seconds of data and ART single-buffer analysis requires 3.5 seconds of data. So the total length of required data is 5 seconds. The following results are obtained.

Asystole—96.8% (722/746) of the asystole cases need only one buffer for a decision. The specificity (% of no shock advised) is 100%. The rest of 3.2% (24/746) asystole cases need the second buffer analysis.

Normal sinus rhythm (NSR)—98.4% (438/445) of the NSR cases need only one buffer for a decision. The specificity (% of no shock advised) is 100%. The rest of 1.6% (7/445) NSR cases need the second buffer analysis.

Organized rhythms and other non-asystole non-shockable rhythms (ORG)—95.1% (1588/1670) of the ORG cases need only one buffer for a decision. The specificity (% of no shock advised) is 100%. The rest of 4.9% (82/1670) ORG cases need the second buffer analysis.

All non-shockable cases (Asystole, NSR and ORG)—96.1% (2748/2861) of the non-shockable cases need only one buffer for a decision. The specificity (% of no shock advised) is 100%. The rest of 3.9% (113/2861) non-shockable cases need the second buffer analysis.

Ventricular fibrillation (VF)—87.1% (532/611) of the VF cases need only one buffer for a decision. The sensitivity (% of shock advised) is 96.2% (512/532). The rest of 12.9% (79/611) VF cases need the second buffer analysis.

Ventricular tachycardia (VT)—70.4% (38/54) of the VT cases need only one buffer for a decision. The sensitivity (% of shock advised) is 97.4% (37/38). The rest of 29.6% (16/54) VT cases need the second buffer analysis.

All shockable cases (VF and VT)—85.7% (570/665) of the shockable cases need only one buffer for a decision. The sensitivity (% of shock advised) is 96.3% (549/570). The rest of 14.3% (95/665) shockable cases need the second buffer analysis.

The exemplary method which uses both algorithms for clean analysis returns results that meet sensitivity and specificity constraints of the current art. Currently a non-shockable rhythm needs around 10 seconds or even longer clean analysis by PAS. By using two algorithms, 96.1% of them only need 5 seconds clean analysis with 100% specificity. Similarly most shockable rhythms also only need 5 second analysis with high sensitivity.

Now turning to FIG. 8, an apparatus is described which incorporates the inventive method. The apparatus comprises a medical device such as an external defibrillator. FIG. 8 illustrates a functional block diagram of an external defibrillator 810 according to the one embodiment of the present invention. Defibrillator 810 is configured as an AED that is intended for use during a cardiac rescue which includes CPR. It is designed for small physical size, light weight, and relatively simple user interface capable of being operated by personnel without high training levels or who otherwise would use the defibrillator 810 only infrequently. Although the present embodiment of the invention is described with respect to application in an AED, other embodiments include application in different types of defibrillators, for example, manual defibrillators, fully automatic defibrillators, and paramedic or clinical defibrillator/monitors.

Defibrillator 810 receives an input 812 of an ECG signal from, for example, two or more electrodes 816 that are connected to a patient. An ECG front end circuit 814 is in electrical communication with the input 812 via a connector plug and socket or the like. The ECG front end circuit 814 operates to amplify, buffer, filter and optionally digitize an electrical ECG signal generated by the patient's heart to produce a stream of digitized ECG samples. The digitized ECG samples are provided to a controller 830, which may be a processor that combines a DSP and ARM processor. One exemplary controller is the family of Applications Processors manufactured by Texas Instruments Incorporated Inc. In one embodiment of the apparatus, the DSP conducts all of the previously described filtering under the ART protocol, and then passes the multiple streams of filtered ECG data to the ARM processor. The ARM buffers the stream of digitized ECG signal data into segments (buffers) corresponding to a predetermined time. The ARM performs an outcomes analysis on the filtered ECG data to detect VF, shockable VT or other shockable rhythms. In accordance with the present invention, the ARM uses the outcomes analysis to determine a treatment regimen which is most beneficial to the patient. These controller 830 portions of the DSP and ARM thus operate together as a first ECG analyzer 831 and a second ECG analyzer 832 as described in the above method steps 602 through 632. Of course, the scope of the present invention is not limited to a particular DSP/ARM configuration. The foregoing and following functions may be equivalently implemented in a single processor or distributed among multiple processors, the processor functions controlled by the automatic execution of software instructions that reside in a memory, such as memory 840.

First ECG analyzer 831 is arranged in communication with input 812. First ECG analyzer 831 is operable to determine a shockable cardiac rhythm during a hands-off period characterized by no presence of CPR-related signal noise artifact from the input. An exemplary ECG analysis algorithm for this first ECG analyzer 831 is PAS, although other similarly-arranged algorithms may be used.

Second ECG analyzer 832 incorporates an analysis algorithm that can determine a shockable rhythm in the presence of CPR-related signal noise artifact. An exemplary second ECG analyzer 832 algorithm is the ART algorithm described previously, or may alternatively comprise the Vrhythm or other artifact-suppressing ECG algorithms. Preferably, the second algorithm has a sensitivity of greater than about 70% and a specificity of greater than about 95% to shockable cardiac rhythms in the presence of CPR compressions-related artifact. This accuracy of the ECG analyzer is sufficient to safely and effectively assess the cardiac state of the input signal in the presence of CPR compressions noise. As with the first ECG analyzer 832, second ECG analyzer 832 is in communication with the input.

Defibrillator 810 further comprises a processor 834 which is in communication with the user interface 818 and both of the first and second ECG analyzers 831, 832. Processor 834 executes software instructions that control the defibrillator to operate in general accordance with the previously described method of FIG. 6. Processor 834 is particularly operable to execute software instructions, such as those stored in memory 840, to control the duration of a hands-off period, and reduce the hands-off period when indicated by analyzers 831, 832. For example, processor 834 may execute software instructions to reduce a duration of the hands-off period only if both of the first and second ECG analyzers 831, 832 determine that a shockable cardiac rhythm is not present. Processor 834 is further operable to execute software instructions to issue a user prompt to end the hands-off period and to resume CPR at the end of the reduced-duration hands-off period.

As previously described in the method 600, the duration of the hands-off period may comprise an initial duration corresponding to two or more sequential ECG buffers. In this embodiment, the first ECG analyzer is operable to determine a shockable cardiac rhythm on each of the ECG buffers. The reduced-duration hands-off period may be the duration of a single ECG buffer used by the first ECG analysis algorithm. In this embodiment, the determination from the first ECG analyzer that a shockable cardiac rhythm is not present is determined from the single ECG buffer. Thus, the user prompts to resume CPR may be issued sooner, resulting in reduced overall hands-off time. CPR prompts may for example be issued five seconds sooner in the case where the hands-off period is about 10 seconds and the reduced-duration hands-off period is about 5 seconds, i.e. two ECG buffers analysis shortened to one ECG buffer analysis. The user prompt in this embodiment may comprise one of a visual prompt and an audible prompt of "no shock advised, start CPR."

Defibrillator 810 may alternatively be arranged according to an alternative operating method in which processor 834 uses a determination from second ECG analyzer 832 which is obtained from a CPR compressions period that occurs just prior to the start of the hands-off period. In this alternative arrangement second ECG analyzer 832 determines during CPR that a shockable cardiac rhythm is not present, and then soon after and during the hands-off period the first ECG analyzer 831 determines that a shockable cardiac rhythm is not present in its first ECG data buffer. The two determinations cause processor 834 to implement a reduced-duration hands-off period which ends at the end of the first ECG data buffer, e.g. at time 707 FIG. 7.

Also as previously described in the inventive method, if one or both ECG analyzers 831, 832 determine that a shockable rhythm is present and the processor 834 determines that a defibrillation shock is indicated, then processor 834, further sends a signal to a HV (high voltage) charging circuit 860 to charge a HV energy storage source 870 in preparation for delivering a shock. When the HV energy storage source 870 is fully charged, processor 834 directs a shock button 892, or 992 on a user interface 918, FIG. 9, to begin flashing via illumination light 920 to re-direct the attention of the user from the task of providing CPR compressions to the task of delivering electrotherapy.

Defibrillator 810 may also convey audible information via a beeper 824. Beeper 824 may, for example, be activated by a device system monitor controller or processor 834 when the HV charger has fully armed the device for delivering a shock, or to help to alert the user to start or stop CPR compressions. Beeper 824 may be aided in these functions by concurrent activation of LED 826 for these conditions.

Figure 9:
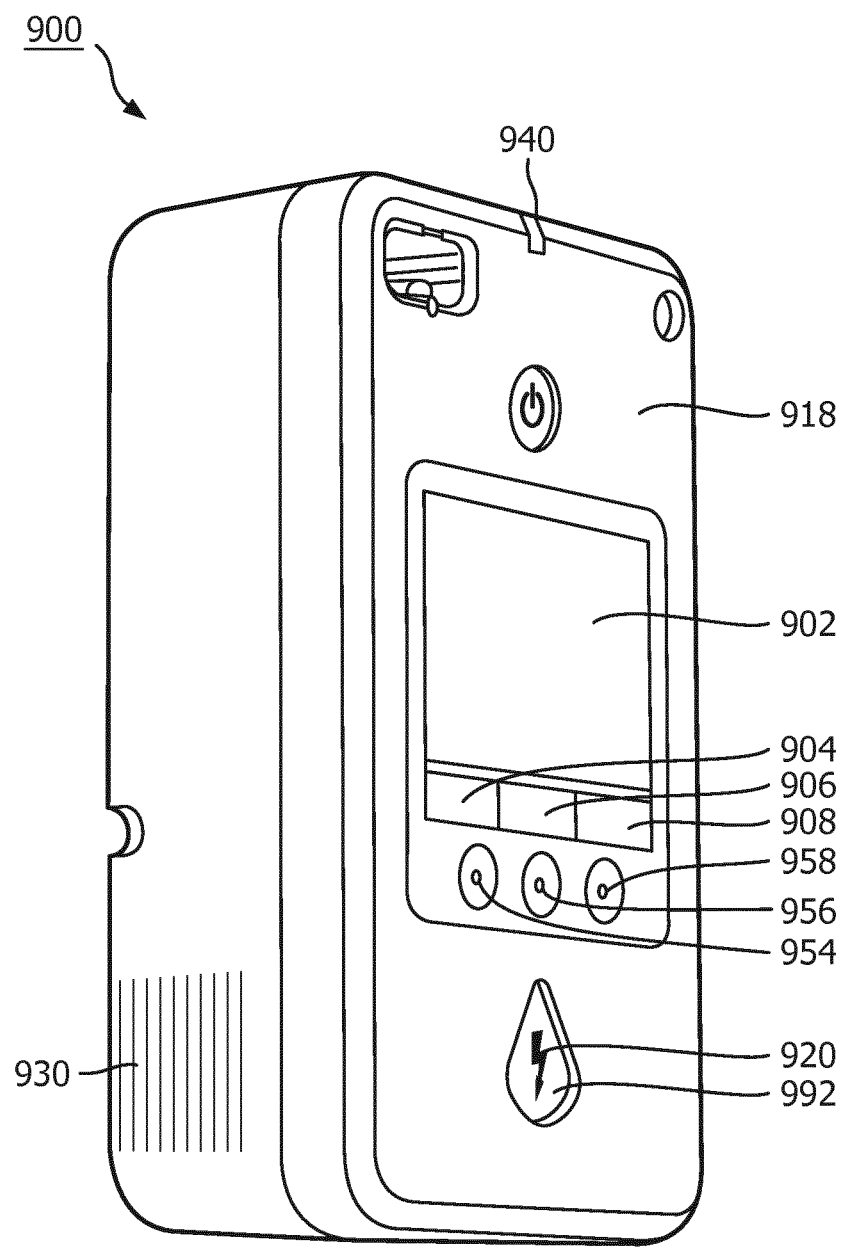
FIG. 9 illustrates a user interface on the external surface of an AED, according to one embodiment of the present invention.

FIG. 9 illustrates a structural embodiment of a defibrillator 900, and in particular a defibrillator user interface 918 on the exterior surfaces of an AED 800 which corresponds generally to the user interface 818 of the FIG. 8 functional block diagram. User interface 918 may include a visual display 902 which provides graphic and textual information pertaining to the state of the cardiac rescue. User interface 918 may also include a speaker 930 which issues aural and audible prompts. An LED 940 may provide a light-based signal for readiness or malfunction. LED 940 structurally corresponds to LED 826 of FIG. 8. User interface 918 may also include first, second and third configurable buttons 954, 956, 958 whose function changes depending on the state of the rescue or on the configuration of the device. The configurable buttons functions may further be indicated by contextual labels 904, 906, 908 displayed on visual display 902. For example, if the device is configured for an advanced operating mode, display 902 may indicate that an adjacent configurable button 954 is configured as an "analyze" button 894. Analyze button 894 may operate to truncate an ongoing rescue protocol. Truncation immediately ceases a CPR period and prepares the defibrillator for immediate delivery of electrotherapy.

Figure 10:
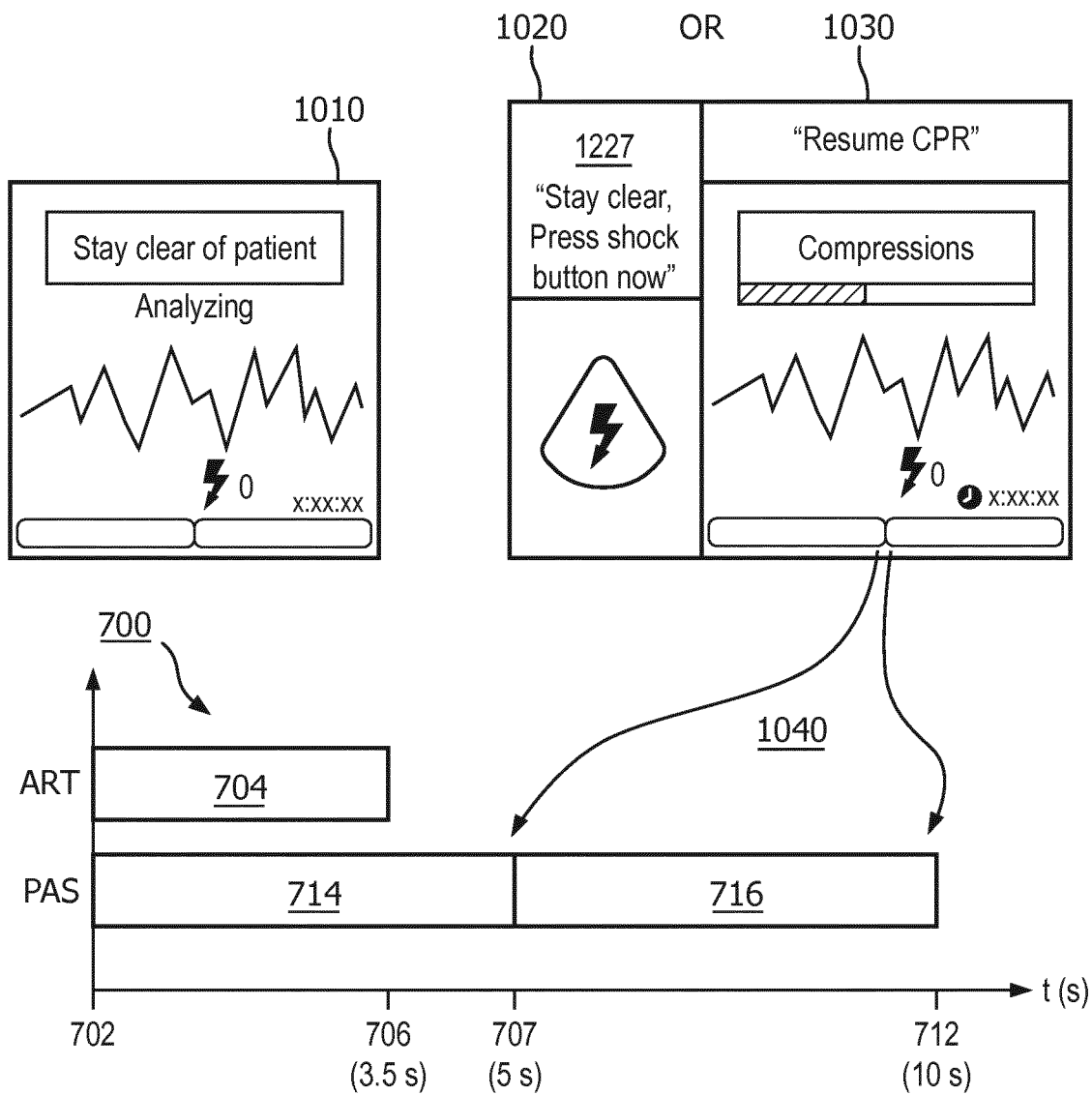
FIG. 10 illustrates exemplary user interfaces for portions of the inventive method according to one embodiment of the present invention.

Turning to FIG. 10, exemplary user interfaces for portions of the inventive method as executed by the apparatus are shown. Just prior to the beginning of the hands-off analysis, user interface 918 may alert the user to stop touching the patient, e.g. "stop CPR", "stay clear of the patient" or the like, by means of the visual display 902. Display 1010 is one example of the visual display 902 at this point in time. The input ECG may be displayed to show whether or not artifact is present on the ECG. The defibrillator 810 may further present a corresponding text message or instruction that it is analyzing, or that CPR compressions are still being detected. Audible instructions and guidance may be issued from speaker 930 which also correspond to the display 1010 instructions as well. LED 940, or beeper 824 may also be used to attract attention to the display.

A visual display 1030 to resume CPR, or a lighted shock button display 1020 is preferably placed on user interface 918 at the end of either the hands-off period or the reduced-length hands-off period. Which display 1030, 1020 and when the display is provided is controlled by processor 834 according to the inventive method. If the hands-off period can be reduced, the appropriate display 1030, 1020 is provided at for example the end of the first ECG analyzer first ECG buffer time. Otherwise the appropriate display 1030, 1020 is displayed at the end of the hands-off period. The time reduction is indicated by the reference number 1040.

Visual display 1030 preferably indicates that CPR should be started or resumed. As shown in 1030, the instruction may be placed on the display, as well as the ECG trace and the state of detected CPR compressions. A timer indication may appear as well. Indications may be accompanied by aural instructions of "No shock advised, start CPR" and flashing lights and beeper sounds as well.

Lighted shock button display 1020 preferably indicates that a shock should be immediately delivered by illuminating the shock button. A corresponding instruction to "Stay clear, press the shock button now" may be placed on visual display 1030 at that time. Also, LED light 826 and beeper 824 may activate to guide the user.

Additional modifications to the device, method, and displays as described above are encompassed within the scope of the invention. For example, various configurations of the user interface displays and aural indicators which fulfill the objectives of the described invention fall within the scope of the claims.

What is claimed is:

1. An automated external defibrillator (AED) for use during cardiopulmonary resuscitation (CPR) comprising:
   an input of an ECG signal of a patient's heart from two or more electrodes in electrical contact with the patient;
   a user interface having at least one of an aural instruction output and a visual display;
   a first ECG analyzer capable of receiving ECG signal data streams from the input and operable to determine, during a hands-off CPR period characterized by no presence of CPR-related signal noise artifact from the input, a shockable cardiac rhythm;
   a second ECG analyzer capable of receiving ECG signal data streams from the input and operable to determine, during a CPR compression period or a CPR hands-off period characterized by a presence of CPR-related signal noise artifact from the input, a shockable cardiac rhythm;

a processor in communication with the user interface, the first ECG analyzer and the second ECG analyzer, the processor operable to execute software instructions to reduce a duration of the hands-off period only if both of the first and second ECG analyzers determine that a shockable cardiac rhythm is not present, wherein the processor is further operable to execute software instructions to issue a user prompt to end the hands-off period and to resume CPR at the end of the reduced-duration hands-off period.

2. The AED of claim 1, wherein the hands-off period comprises an initial duration corresponding to two or more sequential ECG buffers, and wherein the first ECG analyzer is operable to determine a shockable cardiac rhythm on each of the ECG buffers.

3. The AED of claim 2, wherein the reduced-duration hands-off period is a single ECG buffer, and further wherein the first ECG analyzer determination that a shockable cardiac rhythm is not present is determined from the single ECG buffer.

4. The AED of claim 1, wherein the hands-off period is about 10 seconds, and further wherein the reduced-duration hands-off period is about 5 seconds.

5. The AED of claim 1 wherein the user prompt comprises one of a visual prompt and an audible prompt of "No shock advised, start CPR".

6. The AED of claim 1, wherein the second ECG analyzer is operable to determine that a shockable cardiac rhythm is not present during a CPR compressions period that occurs just prior to the hands-off period.

7. The AED of claim 1, wherein the second ECG analyzer is operable to determine that a shockable cardiac rhythm is not present during the hands-off period.

8. A method for controlling a defibrillator during the application of cardiopulmonary resuscitation (CPR), comprising the steps of:

providing a defibrillator having a first ECG analyzer operable to determine, during a hands-off CPR period characterized by no presence of CPR-related signal noise artifact, a shockable cardiac rhythm, and a second ECG analyzer operable to determine, during a CPR compression period or a CPR hands-off period, in the presence of CPR-related signal noise artifact, a shockable cardiac rhythm;

receiving an ECG signal data stream from two or more external electrodes in electrical contact with a patient and in communication with the first and second ECG analyzers, the ECG signal data comprising a cardiac signal;

prompting with one of an audible or visual output instructions for providing successive periods of CPR wherein the ECG signal is characterized by corruption from a CPR compressions noise artifact and hands-off periods wherein the ECG signal is characterized by a lack of CPR compressions noise artifact;

analyzing the cardiac signal with the first ECG analyzer during at least one CPR hands-off period characterized by a duration;

analyzing the cardiac signal with the second ECG analyzer;

reducing the duration of the hands-off period to a reduced-duration hands-off period only if both of the first and second ECG analyzers determine that a shockable cardiac rhythm is not present; and issuing with one of the audible or visual output, instructions for ending the hands-off period and for resuming CPR at the end of the reduced-duration hands-off period.

9. The method of claim 8, wherein the hands-off period consists of two or more ECG data buffers each of a predetermined length, and wherein the reduced-duration hands-off period is one ECG data buffer.

10. The method of claim 8, wherein the hands-off period is about ten seconds in length, and wherein the reduced-duration hands-off period is about five seconds in length.

11. The method of claim 8, wherein the issuing step occurs immediately at the end of the reduced-duration hands-off period.

12. The method of claim 11, wherein the issuing step comprises a voice prompt of "No shock advised, start CPR".

13. The method of claim 8, wherein the analyzing the cardiac signal with the second ECG analyzer step occurs during a CPR compressions period that occurs just prior to the hands-off period.

14. The method of claim 8, wherein the analyzing the cardiac signal with the second ECG analyzer step occurs during the hands-off period.

* * * * *